United States Patent
Lowe

[11] Patent Number: 5,906,175
[45] Date of Patent: May 25, 1999

[54] CONTROLLED ASEXUAL PROPAGATION OF CERTAIN MARINE INVERTEBRATES BY MEANS OF SEGMENTAL TRANSPLANTATION

[76] Inventor: Alan S. Lowe, 25 Collingwood Ct., Palm Coast, Fla. 32135

[21] Appl. No.: 08/897,486

[22] Filed: Jul. 21, 1997

Related U.S. Application Data

[60] Provisional application No. 60/022,773, Jul. 30, 1996.
[51] Int. Cl.⁶ ..................................................... A01K 61/00
[52] U.S. Cl. ......................... 119/200; 119/221; 119/234; 119/6.7
[58] Field of Search ............................ 119/200, 6.7, 221, 119/234

[56] References Cited

U.S. PATENT DOCUMENTS 5,564,369  10/1996  Barber et al. ........................... 119/221

FOREIGN PATENT DOCUMENTS 406169666  6/1994  Japan ..................................... 119/200

Primary Examiner—Michael J. Carone
Assistant Examiner—James S. Bergin
Attorney, Agent, or Firm—Sughrue, Mion, Zinn, Macpeak & Seas, PLLC

[57] ABSTRACT

A methodology for the asexual propagation of a plurality of species of substantially sedentary marine invertebrates which naturally attach to or hold fast to a support where propagation is achieved by employment of segmentation and transplantation which is accomplished by intentionally forced segmentation of a predeterminable portion of the invertebrate's tissue and where the segmented tissue is manipulated to become substantially attached to a suitable support by a temporary holding device thereby resulting in a condition where the primary invertebrate as well as the propagated invertebrate can survive independently of one another.

14 Claims, 7 Drawing Sheets

5,906,175

CONTROLLED ASEXUAL PROPAGATION OF CERTAIN MARINE INVERTEBRATES BY MEANS OF SEGMENTAL TRANSPLANTATION

This application claims priority benefits under 35 U.S.C. §119 of provisional application 60/022,773, filed Jul. 30, 1996.

BACKGROUND

1. Field of Invention

This invention relates to a methodology for asexual propagation of a plurality of species of substantially sedentary marine invertebrates that hold fast or naturally attach to a support. Propagation is achieved by means of segmental transplantation which is accomplished by intentionally forced segmentation of a predeterminable portion of an invertebrate's tissue. The segmented tissue is manipulated to become substantially attached to a suitable support thereby resulting in a condition where the primary invertebrate as well as the propagated invertebrate can survive independently of one another.

2. Description of Prior Art

For many years there has been substantially unrestrained and unregulated harvesting of many live marine invertebrates from ocean reefs in all parts of the world to satisfy individual, commercial, pharmaceutical and industrial needs. The impact of this indiscriminate gathering has exacted a severe toll on these fragile marine ecosystems. Damage inflicted by ship's hulls and even anchors is also causing grave concern among environmentalists and international political bodies. In addition to the devastation of the reefs due to human interaction, damage is being done by storms and environmental change. There is a global realization that these marine resources are finite and unless the destruction stops, our "underwater rain forests" will cease to exist. Estimates done by N.O.A.A. and other marine biologists indicate that as of 1995, ten percent of the world's reefs had been destroyed beyond repair, and that in another ten years said percentage will increase to forty percent. If nothing is done, N.O.A.A. estimates that all reefs could be gone in as little as twenty years.

The methodology of this invention is an efficient way to asexually propagate a plurality of substantially sedentary marine invertebrate species to substantially satisfy the needs of industry without continuing to damage the natural reefs through harvesting. The propagated invertebrates can also restock damaged, dead or dying ocean reefs. Through controlled experimentation and testing the concepts and techniques of this invention have been proven to be practicable, successful and have resulted in an ability to asexually propagate substantially sedentary marine invertebrates at a rate and in a manner which is methodical, controlled and substantially accelerated beyond the invertebrates' normal rates of reproduction in nature.

BRIEF SUMMARY OF THE INVENTION

Besides the known advantages of asexual propagation of a plurality of species of substantially sedentary marine invertebrates that naturally attach to or hold fast to a support by means of segmental transplantation, as heretofore described, several advantages of this present invention are:

(a) to provide a plurality of said propagated invertebrates where a plurality of individual segmented specimens can be derived from a single primary invertebrate;

(b) to provide a means for said propagated invertebrates to successfully reproduce in numbers and at rates that are substantially accelerated beyond an invertebrate's normal rate of reproduction in nature;

(c) to provide a means for a plurality of invertebrates to be propagated in a manner which is methodical and controlled;

(d) to provide a means for propagated invertebrate specimens to be substantially attached to a manufactured support where the support can be any one of a plurality of shapes and designs according to the intended end use of the propagated invertebrate such as but not limited to, a support designed for those propagated invertebrates whose end use is reef restocking and another support designed for those propagated invertebrates whose end use is intended to be the global aquarium trade and another support designed where the invertebrates' end use will be related to research;

(e) to provide a means via a manufactured support for ease in identifying that the propagated invertebrate was not removed from a natural reef, thereby aiding, for example, an agency of a government that is charged with the task of inspecting sellers and users of wildlife where legislation may exist prohibiting the unauthorized taking, trade or possession of an invertebrate from nature.

Further advantages of asexual propagation of a plurality of species of substantially sedentary marine invertebrates that naturally attach to or hold fast to a support by means of segmental transplantation include that propagation can be achieved economically and is environmentally favorable.

DRAWING REFERENCE NUMERALS

Figure 1A:
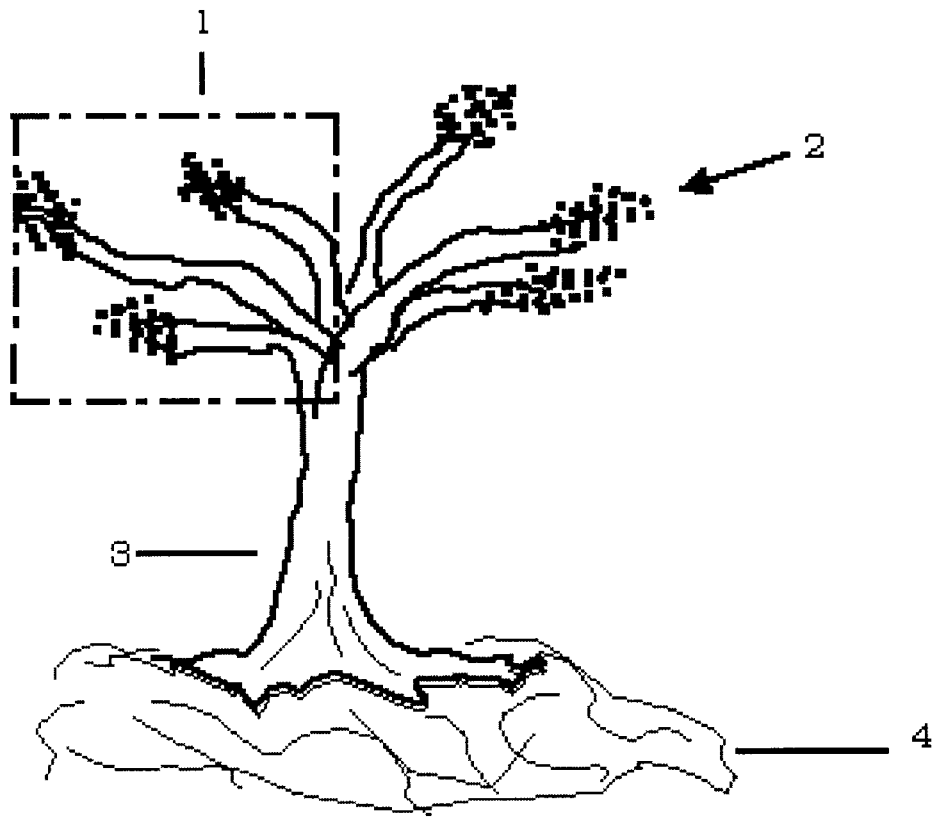
FIG. 1A—View comprising a selected area of a plurality of potentially severable appendages which can be transplanted and is the subject matter of FIG. 1B.
Figure 1B:
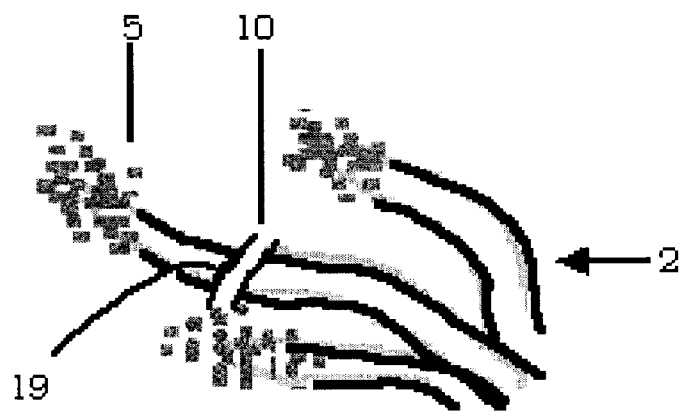
FIG. 1B—View comprising area 1 of FIG. 1A. including a segmented specimen.

1—View, comprising a selected area of a plurality of potentially severable appendages which can be transplanted and is the subject matter FIG. 1B.
2—Appendages, branches.
3—Body, trunk.
4—Substrate, base, support, to which a invertebrate substantially attaches itself in nature.
5—Segmented portion, bud. specimen.
6—Temporary holding device.
7—Manufactured support.
8—Crown, cap.
9—Overhanging brim of crown with no trunk attachment.
10—Division line shown for clarification only.
11—Crown area still attached to trunk.
12—Segmented specimen of overhanging crown brim with no trunk attachment.
13—New growth of trunk, body, stem.
14—Colonial polyps of encrusting invertebrate.
15—Interconnecting tissue of colonial polyps.
16—New budding growth.
17—Area of interconnecting tissue to be segmented.
18—Specimen of independent invertebrate asexually propagated by means of segmental transplantation.
19—Segmented Tissue.
20—Crown invertebrate substantially attached to a manufactured base.

DESCRIPTION AND OPERATION OF FIGS. 1A–3E

Figure 2A:
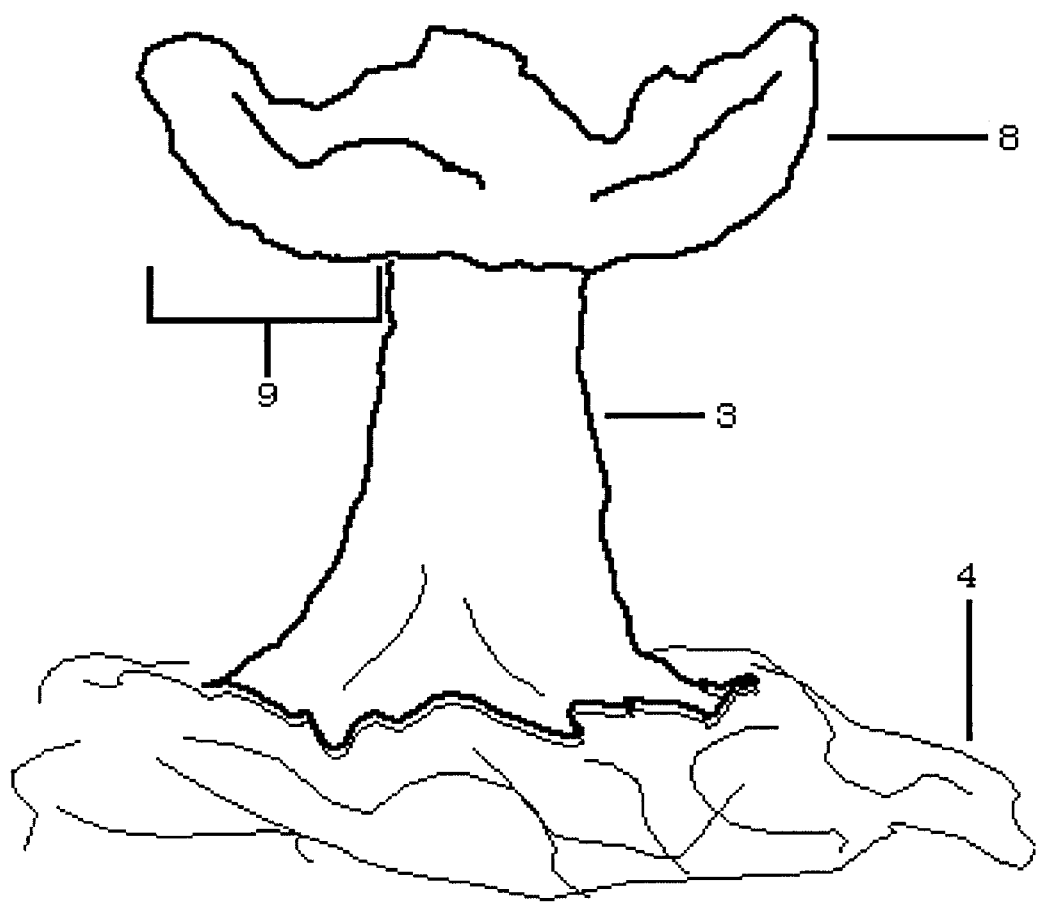
FIG. 2A—View depicting a plurality of components of one example of a plurality of substantially sedentary invertebrate.
Figure 3A:
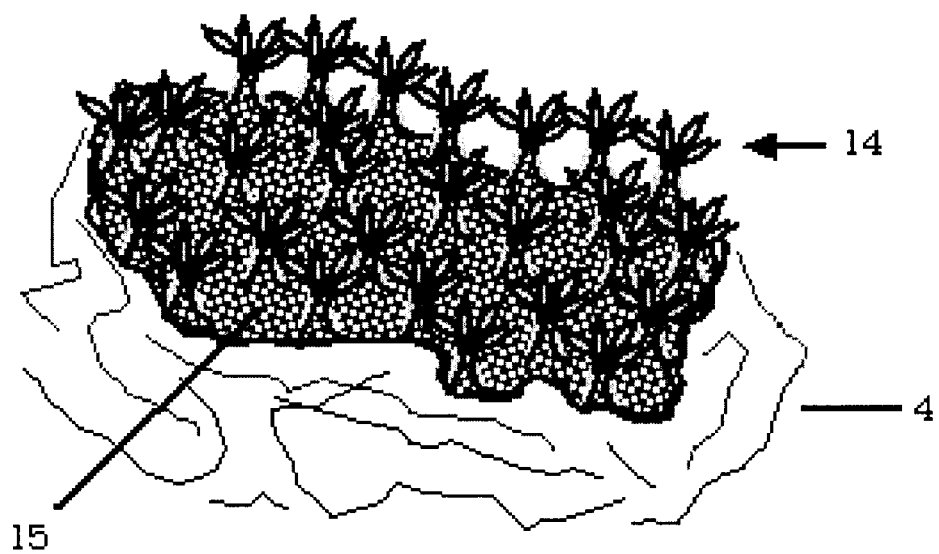
FIG. 3A—View showing one example of a plurality of substantially sedentary encrusting invertebrates.

The Figures of this patent are of no particular scale as the subject matter is a process involving live organisms and said organism's size is subject to change. Typical examples of the plurality of species of substantially sedentary marine invertebrates which naturally attach to or hold fast to a suitable support are illustrated in FIGS. 1A, 2A, and 3A.

In FIG. 1A, the depicted example is of the species Cladiella and is used only to depict a substantially sedentary invertebrate having branches. The ability to propagate invertebrates utilizing segmental transplantation is not limited to this species.

FIG. 1A is an example of a heretofore mentioned invertebrate comprising numerous appendages 2 of varying lengths attached to a trunk like body 3 which is substantially attached in nature to a rock base or other suitable support 4. The sectional area 1 shows an embodiment of a selected area of a plurality of potentially severable appendages having been chosen because they are of a length making the appendages easy to manipulate for segmentation.

The selected area 1 (FIG. 1A), is blown up in FIG. 1B depicting suitable specimens of living tissue appendages 2 and where a portion of said specimen has been segmented, detached, from the heretofore mentioned primary invertebrate. Segmentation is accomplished by locating a suitable specimen and forcing it to be intentionally severed from the primary invertebrate's tissue 19 by means of a suitable cutting or clamping device designed for the purpose of segmenting tissue resulting in a specimen 5 being physically detached 10 from the tissue of the primary invertebrate's selected appendage in a manner enabling the primary invertebrate and the segmented tissue 5 to survive the segmentation procedure.

Figure 1C:
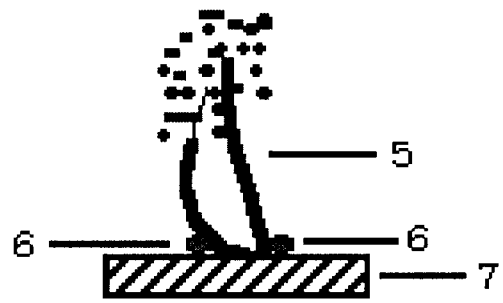
FIG. 1C—View showing the arrangement of the FIG. 1B segmented specimen which is held in place by a temporary retaining device and where said specimen is upon a suitable support.

Subsequent to segmentation (FIG. 1C) the detached specimen 5 is temporarily held substantially motionless and in contact with a suitable support 7 by means of a temporary holding device 6 where the device causes substantially no damage to the tissue and until such time as the specimen 5 substantially attaches to its support 7.

Figure 1D:
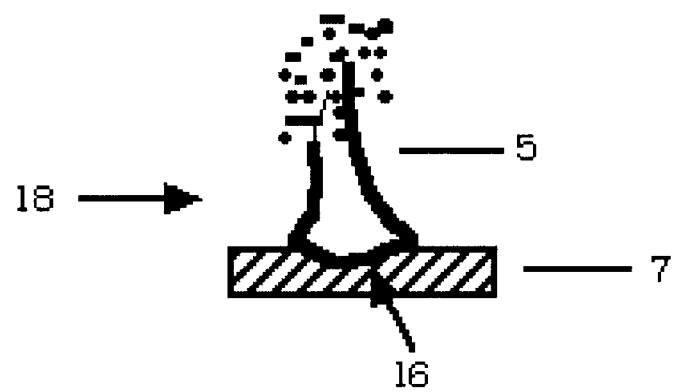
FIG. 1D—View showing the segmented specimen of FIG. 1A. where said specimen has attached to a suitable support and where the temporary holding device has been removed.

Subsequent to specimen 5 substantially attaching to support 7 (FIG. 1D), attachment can be determined by loosening the temporary holding device 6 and observing any unanticipated movement on part of specimen 5 or through observation of new growth 16 which is in itself attached to said support 7. Then the holding device 6 is removed. The result of this process is an asexually propagated invertebrate 18 by means of intentionally forced segmental transplantation where the invertebrate 18 is substantially independent of the primary invertebrate.

An example of a plurality of species of substantially sedentary marine invertebrates which naturally attach to or hold fast to a suitable support which unlike the specimen example illustrated in FIG. 1A do not have apparent multiple appendages suitable for segmentation is illustrated in FIG. 2A. The depicted example is of the species Sarcophyton and is used only to depict a substantially sedentary invertebrate having a crown. The ability to propagate invertebrates utilizing segmental transplantation is not limited to this species.

Figure 2B:
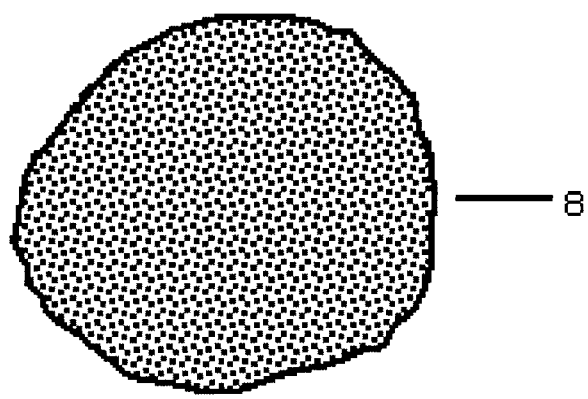
FIG. 2B—View looking down upon the crown of the invertebrate depicted in FIG. 2A.
Figure 2C:
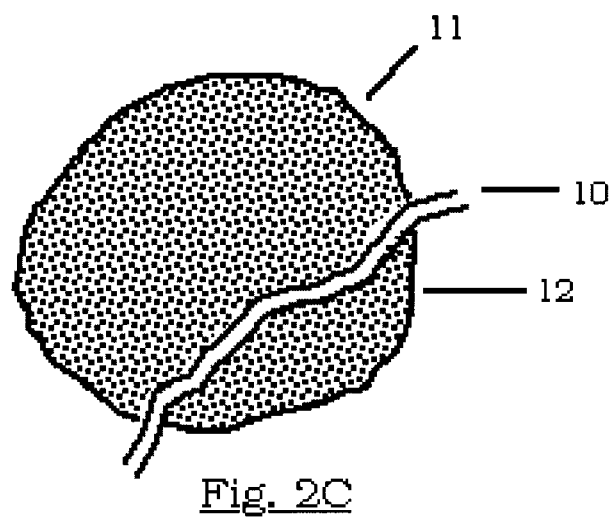
FIG. 2C—View looking down upon the crown of the invertebrate depicted in FIG. 2A including an area of said crown which has been segmented.

The methodology for segmental transplantation of said FIG. 2A invertebrate is substantially the same as heretofore outlined for a FIG. 1A invertebrate where segmentation is accomplished by means of locating a suitable overhanging portion 9 of the invertebrate's crown 8 (FIGS. 2A and 2B) and forcing it to be intentionally severed from the primary invertebrate's tissue (FIG. 2C) by means of a suitable cutting or clamping device designed for the purpose of segmenting tissue, resulting in a specimen 12 being physically detached at division line 10 from the tissue of the primary invertebrate's crown area 11 in a manor enabling the primary invertebrate and the segmented tissue 5 to survive the segmentation procedure.

Figure 2D:
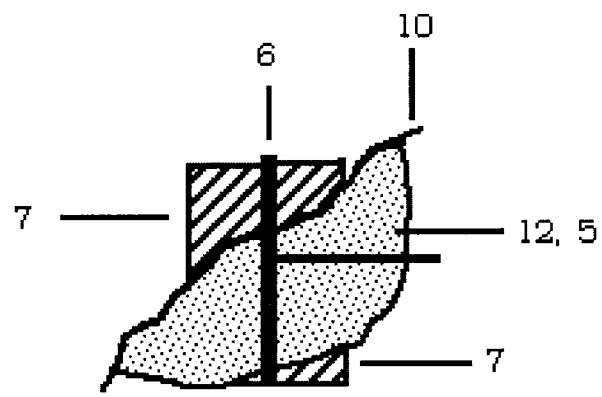
FIG. 2D—View looking down upon the segmented specimen of FIG. 2C which has been restrained upon a suitable base so as to attach thereto.
Figure 2E:
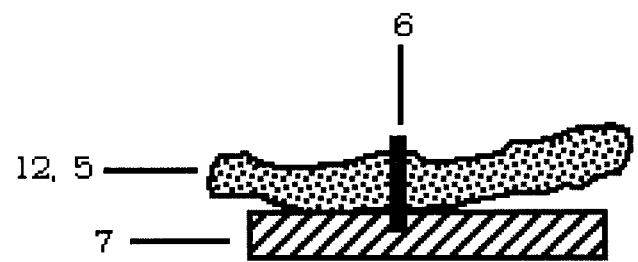
FIG. 2E—View from a side of the segmented specimen of FIG. 2C which has been restrained upon a suitable base so as to attach thereto.
Figure 2F:
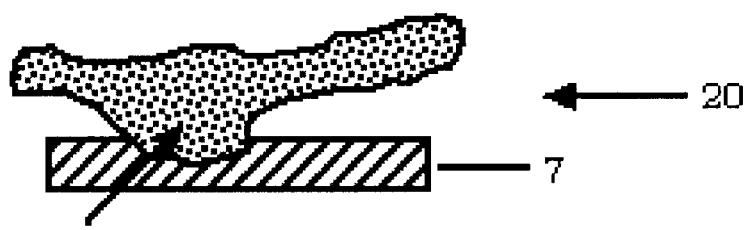
FIG. 2F—View from the side of the segmented specimen of FIG. 2C having been substantially attached to a suitable support and having the temporary holding device removed.

The segmented specimen 12 is caused to be substantially attached to a suitable base 7 in a manner that is substantially similar to the process heretofore described where such attachment is illustrated in FIGS. 2D, 2E and 2F.

An example of a plurality of species of substantially sedentary marine invertebrates which naturally attach to or hold fast to a suitable support which unlike the specimen example illustrated in FIG. 1A do not have multiple appendages suitable for segmentation and unlike the specimen example illustrated in FIG. 2A do not have a crown is illustrated if FIG. 3A. The depicted example in FIG. 3A is of the species Xenia and is shown only to depict a substantially sedentary encrusting invertebrate. The ability to propagate invertebrates utilizing segmental transplantation is not limited to the species Xenia.

Figure 3B:
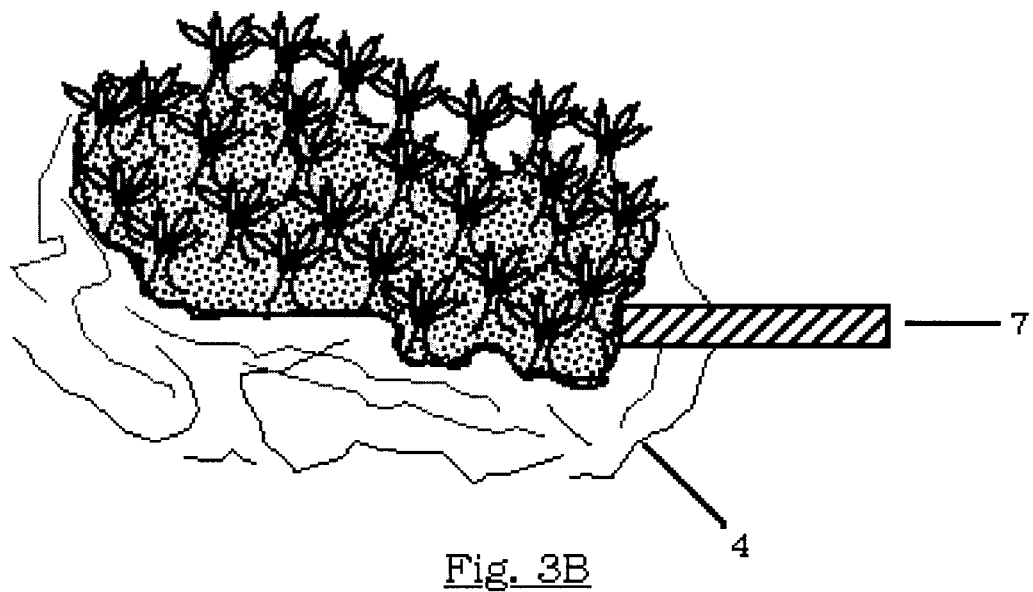
FIG. 3B—View depicting a suitable support being positioned so as to be substantially motionless and in constant contact with the invertebrate.
Figure 3C:
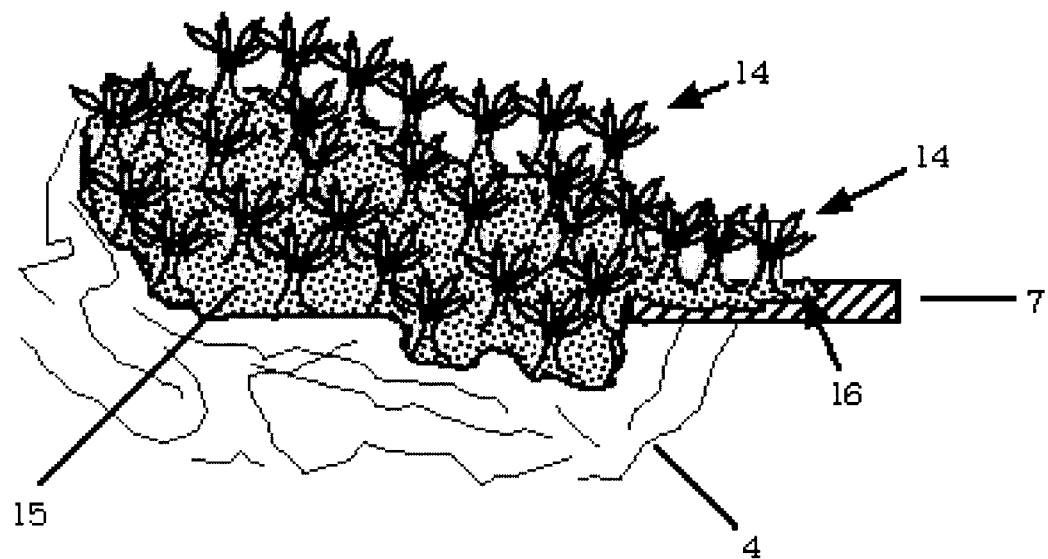
FIG. 3C—View showing tissue substantially attaching to a FIG. 3B suitable support.

The methodology for segmentation and transplantation of said FIG. 3A invertebrate is substantially the same as heretofore outlined. The connecting tissue 15 which connects the polyps 14 is caused to be substantially attached to a suitable support 7 (FIG. 3B) by means of placing a support 7 in constant and substantially motionless contact with connecting tissue 15 until the connecting tissue suitably attaches to the support. Determination of proper attachment of connecting tissue (FIG. 3C) to support 7 is as heretofore described.

Figure 3D:
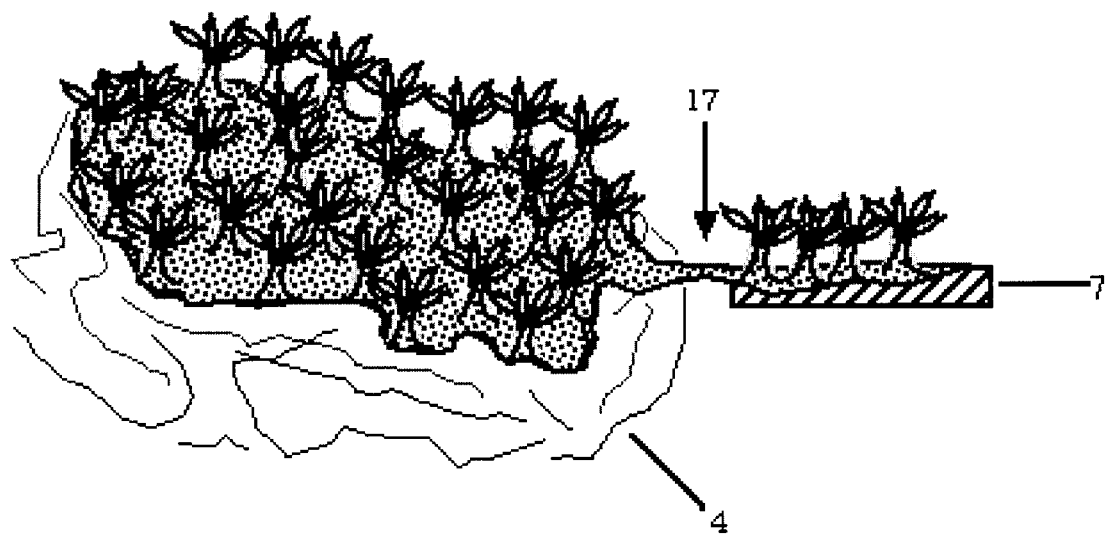
FIG. 3D—View depicting a primary invertebrate and a FIG. 3B suitable support having been encrusted as well as depicting the connecting tissue between said support and primary invertebrate.
Figure 3E:
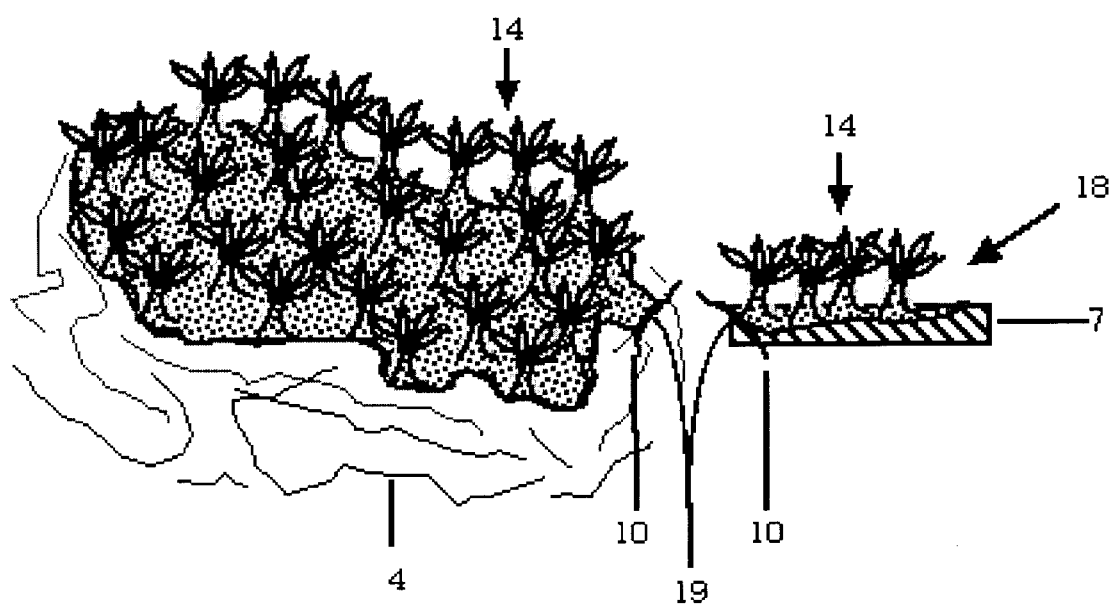
FIG. 3E—View depicting the severed connecting tissue depicted in FIG. 3D.

Subsequent to determination of satisfactory tissue attachment, the support 7 is manipulated to allow access to the connecting tissue 17 (FIG. 3D) which is bridging the specimen substantially attached to support 7 and the primary invertebrate substantially attached to support 4. The methodology for segmenting connecting tissue 17 is substantially the same as described for a FIG. 1A invertebrate where segmentation is accomplished by means of locating the connecting tissue 17 and forcing it to be intentionally severed from the primary invertebrate's tissue (FIG. 3E) by means of a suitable cutting or clamping device designed for the purpose of segmenting tissue, resulting in a specimen 18 being physically detached from the primary invertebrate's tissue 19 in a manner enabling the primary invertebrate and the segmented specimen 18 to survive the segmentation procedure.

SUMMARY, RAMIFICATIONS AND SCOPE

Accordingly, the reader will understand that the process of asexual propagation by means of segmental transplantation can be accomplished with a plurality of species of substantially sedentary marine invertebrates which naturally attach to or hold fast to a suitable support. The concepts and techniques of this invention have been proven to be practicable, successful, environmentally friendly and have resulted in the ability to asexually propagate a plurality of substantially sedentary marine invertebrates at a rate and in a manner which is methodical, controlled and substantially accelerated beyond said invertebrate's normal rate of reproduction in nature. Furthermore, asexual propagation by means of segmental transplantation has added advantages in that:

it provides a plurality of propagated invertebrates where a plurality of individual segmented specimens can be derived from a single primary invertebrate;

it provides a means for propagated invertebrates to be successfully reproduced in numbers and at a rate which is accelerated beyond the invertebrate's normal rate of reproduction in nature;

it provides a means for a plurality of invertebrates to be propagated in a manner which is methodical and controlled;

it is an efficient way to asexually propagate a plurality of substantially sedentary marine invertebrates which naturally attach to or hold fast to a suitable support;

it provides a means for propagation which can be achieved economically and is environmentally favorable;

it provides a means to substantially satisfy the needs of a plurality of industries without continuing to damage natural reefs through the harvesting thereof;

it permits a stock of propagated invertebrates to be created which can be utilized to restock damaged, dead or dying ocean reefs;

it provides a means for propagated invertebrate specimens to be substantially attached to a manufactured support where the support can be of a plurality of shapes and designs according to the intended end use of propagated invertebrate;

Although the outline above contains a plurality of specifications, these should not be construed as limiting the scope of the invention but as merely providing illustrations of some of the presently preferred embodiments of this invention. For example, it provide a means via said manufactured support for ease in identifying that the propagated invertebrate was not removed from a natural reef, thus aiding an agency of a government where the agency is charged with the task of inspecting sellers and users of wildlife, especially where legislation may prohibit the unauthorized taking, trade or possession of invertebrate from nature.

Thus the scope of the invention should be determined by the appended claims and their legal equivalents, rather than by the examples given.

I claim:

1. A method for asexually propagating a species of substantially sedentary marine invertebrates that naturally attach or hold fast to a support, said method comprising:

(a) segmenting by artificial force, a determinable portion of living tissue of a primary invertebrate to produce a segment segmented from the primary invertebrate's tissue to create at least one segmented specimen of living tissue wherein said segmented specimen embodies all necessary living components enabling it to survive and said segmenting enables the primary invertebrate to survive; and (b) manipulating said segmented specimen of living tissue to become substantially attached to a support material enabling said segmented specimen to survive independently from the primary invertebrate.

2. The method of claim 1, wherein said segmented specimen is of a size adequate to be manipulated.

3. The method of claim 1, wherein segmenting is accomplished by locating said specimen and severing said specimen from the primary invertebrate's tissue by means of a cutting or clamping device, said segmenting resulting in said specimen becoming physically detached from the tissue of the primary invertebrate and enabling the primary invertebrate and the segmented tissue to survive the segmenting.

4. The method of claim 1, wherein said support material is an inert substance formed to have dimensions which can be adequately manipulated and which will allow said segmented specimen attached thereupon to survive.

5. The method of claim 4 wherein said support material is identifiable as a synthetic material by at least one indicator selected from the group consisting of a mark, arrangement, composition and certification, so as to allow an invertebrate attached thereupon to be identifiable as a propagated invertebrate.

6. The method of claim 1, wherein said manipulating said segmented specimen includes physically holding said specimen being physically held, motionless and in constant contact with said support with a device capable of holding said specimen in contact with said support while causing substantially no damage to said specimen, said holding continuing until such time as said specimen substantially attaches to said support.

7. The method of claim 1, wherein said method reproduces a plurality of substantially sedentary marine invertebrates in a manner which is substantially accelerated beyond said species' natural rate of reproduction.

8. A method of asexually propagating a species of substantially sedentary marine invertebrates that naturally attach or hold fast to a support, said method comprising:

(a) arranging a support of suitable material to allow said support to be held temporarily motionless and in contact with a first portion of the living tissue of a primary invertebrate and maintaining said support in place for a sufficient duration of time so as to cause said primary invertebrate's tissue to attach to a suitable area of said support thereby forming an attached portion and a bridging portion of said primary invertebrate, said bridging portion bridging said first portion and said attached portion; and (b) severing, by cleaving said bridging portion with artificial force, to cause said support and said attached portion to be physically detached from the tissue of the first portion of said primary invertebrate and enabling the primary invertebrate and the attached portion to survive.

9. The method of claim 8, wherein said support is an inert substance formed to have dimensions which can be adequately manipulated and which will allow said attached portion to survive after severing.

10. The method of claim 9, wherein said support is identifiable as a synthetic material by at least one indicator selected from the group consisting of a mark, arrangement, composition and certification, so as to allow a propagated invertebrate attached thereupon to be identifiable as a propagated invertebrate.

11. The method of claim 8, wherein said severing of said bridging portion includes locating said tissue and causing it to be severed by means of a cutting or clamping device, said support and attached portion being physically separated from the first portion enabling the primary invertebrate and the attached portion attached to said support to survive.

12. The method of claim 8, wherein said method reproduces a plurality of substantially sedentary marine invertebrates in a manner which is substantially accelerated beyond said species' natural rate of reproduction.

13. A platform for propagation of a species of substantially sedentary marine invertebrates comprising:

a) a support identifiable as a synthetic material by at least one indicator selected from the group consisting of a mark, arrangement, composition and certification, so as to allow a propagated invertebrate attached thereupon to be identifiable as a propagated invertebrate; and b) a specimen of living tissue of a species of substantially sedentary marine invertebrates that naturally attaches to or holds fast to a support said specimen attached to or held fast to said support, and said specimen embodying all necessary living components for said specimen to be able to survive when detached from tissue of a primary invertebrate that was a source for asexual propagation of said specimen.

14. The composition of claim 13, wherein said specimen has been cleaved from said primary invertebrate.

* * * * *